(12) United States Patent
Bublitz et al.

(10) Patent No.: US 10,582,852 B2
(45) Date of Patent: Mar. 10, 2020

(54) METHOD AND APPARATUS FOR REDUCING SCATTERED LIGHT IN BROAD-LINE FUNDUS IMAGING

(71) Applicant: Carl Zeiss Meditec AG, Jena (DE)

(72) Inventors: Daniel Bublitz, Rausdorf (DE); Lothar Müller, Ottendorf (DE); Andrea Berner, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 15/548,393

(22) PCT Filed: Feb. 3, 2016

(86) PCT No.: PCT/EP2016/052287
§ 371 (c)(1),
(2) Date: Aug. 2, 2017

(87) PCT Pub. No.: WO2016/124644
PCT Pub. Date: Aug. 11, 2016

(65) Prior Publication Data
US 2018/0014727 A1    Jan. 18, 2018

Related U.S. Application Data

(60) Provisional application No. 62/112,583, filed on Feb. 5, 2015.

(51) Int. Cl.
*A61B 3/14* (2006.01)
*A61B 3/12* (2006.01)
*A61B 3/15* (2006.01)

(52) U.S. Cl.
CPC .............. *A61B 3/1208* (2013.01); *A61B 3/12* (2013.01); *A61B 3/14* (2013.01); *A61B 3/156* (2013.01)

(58) Field of Classification Search
CPC .............................. A61B 3/1208; A61B 3/156
USPC ......................................... 351/205, 206, 246
See application file for complete search history.

(56) References Cited

U.S. PATENT DOCUMENTS

| 4,135,791 A | 1/1979 | Govignon |
| 4,170,398 A | 10/1979 | Koesterm |
| 4,732,466 A | 3/1988 | Humphrey |
| 5,120,123 A | 6/1992 | Akiyama |

(Continued)

FOREIGN PATENT DOCUMENTS

| EP | 2422692 A1 | 2/2012 |
| EP | 2364429 B1 | 3/2013 |

(Continued)

OTHER PUBLICATIONS

International Preliminary Report on Patentability and Written Opinion received for PCT Patent Application No. PCT/EP2016/052287, dated Aug. 17, 2017, 8 pages.

(Continued)

*Primary Examiner* — James R Greece
(74) *Attorney, Agent, or Firm* — Morrison & Foerster LLP

(57) ABSTRACT

Methods and apparatuses for fundus imaging are presented that use sequential selective illumination patterns to suppress unwanted reflections, scattering and haze from various optical components of a fundus-viewing instrument. This is particularly the case with those unwanted reflections produced by the objective lens contained within said instrument.

20 Claims, 8 Drawing Sheets

(56) References Cited

U.S. PATENT DOCUMENTS

| | | | |
|---|---|---|---|
| 5,455,644 A | 10/1995 | Yazawa et al. | |
| 5,500,697 A | 3/1996 | Fujiedam | |
| 5,943,116 A * | 8/1999 | Zeimer | A61B 3/0058 351/221 |
| 7,456,949 B2 * | 11/2008 | Somani | A61F 9/008 250/252.1 |
| 7,854,510 B2 | 12/2010 | Verdooner et al. | |
| 8,488,895 B2 | 7/2013 | Muller et al. | |
| 8,814,362 B2 | 8/2014 | Verdooner | |
| 8,967,806 B2 | 3/2015 | Bublitz et al. | |
| 9,456,746 B2 | 10/2016 | Bublitz et al. | |
| 2004/0051847 A1 * | 3/2004 | Vilser | A61B 3/10 351/159.73 |
| 2006/0092376 A1 * | 5/2006 | Baek | A61B 3/145 351/213 |
| 2006/0114411 A1 | 6/2006 | Wei et al. | |
| 2007/0030446 A1 | 2/2007 | Su et al. | |
| 2007/0031002 A1 | 2/2007 | Venkatesh et al. | |
| 2007/0081127 A1 | 4/2007 | Liang et al. | |
| 2007/0091264 A1 * | 4/2007 | Kahlen | A61B 5/1171 351/206 |
| 2009/0153797 A1 | 6/2009 | Allon et al. | |
| 2010/0097573 A1 * | 4/2010 | Verdooner | A61B 3/14 351/206 |
| 2010/0309431 A1 | 12/2010 | Itoh et al. | |
| 2011/0176107 A1 * | 7/2011 | Yoshida | A61B 3/102 351/206 |
| 2011/0234977 A1 * | 9/2011 | Verdooner | A61B 3/102 351/207 |
| 2012/0229617 A1 | 9/2012 | Yates et al. | |
| 2013/0222763 A1 | 8/2013 | Bublitz et al. | |
| 2013/0335706 A1 * | 12/2013 | Schmitt-Manderbach | A61B 3/1005 351/221 |
| 2014/0218687 A1 | 8/2014 | Verdooner | |
| 2015/0131050 A1 * | 5/2015 | Bublitz | A61B 3/12 351/206 |

FOREIGN PATENT DOCUMENTS

| | | |
|---|---|---|
| JP | 2004-522488 A | 7/2004 |
| JP | 2009-285108 A | 12/2009 |
| JP | 2013-527775 A | 7/2013 |
| WO | 2002/053020 A2 | 7/2002 |
| WO | 2012/059236 A1 | 5/2012 |
| WO | 2014/140256 A2 | 9/2014 |

OTHER PUBLICATIONS

International Search Report and Written Opinion received for PCT Patent Application No. PCT/EP2016/052287, dated Apr. 14, 2016, 10 pages.

Sulai, et al., "Visualization of Retinal Vascular Structure and Perfusion with a Nonconfocal Adaptive Optics Scanning Light Ophthalmoscope", Optical Society of America, vol. 31, No. 3, Mar. 2014, pp. 569-579.

Office Action received for Japanese Patent Application No. 2017-540162, dated Nov. 19, 2019, 7 pages (4 pages of English Translation and 3 pages of Official Copy).

\* cited by examiner

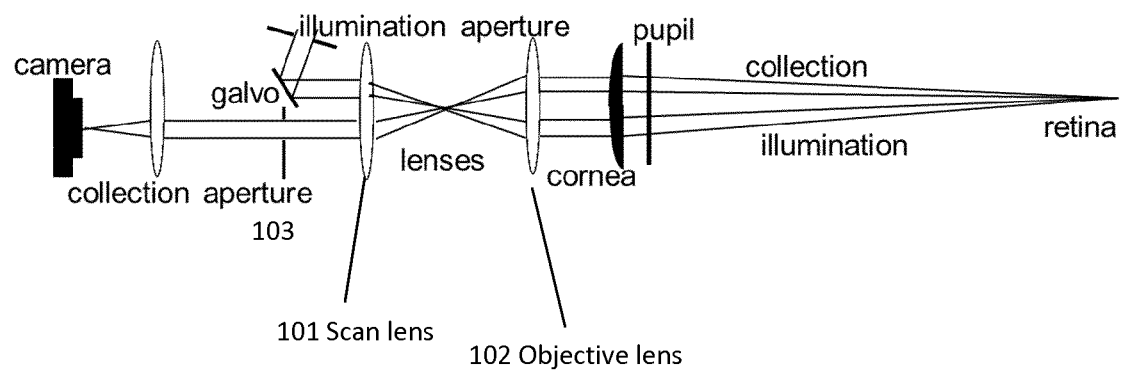
Figure 1a (Prior Art)
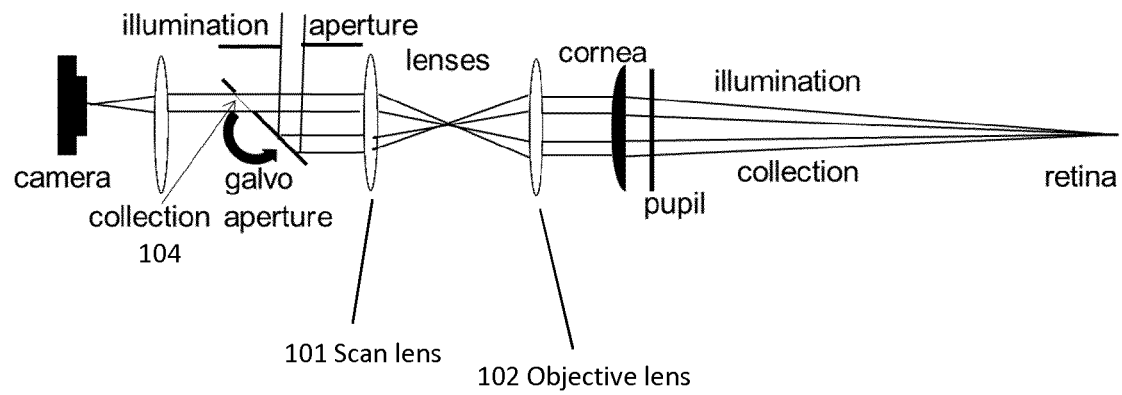
Figure 1b (Prior Art)
Figure 1

FIGURE 3
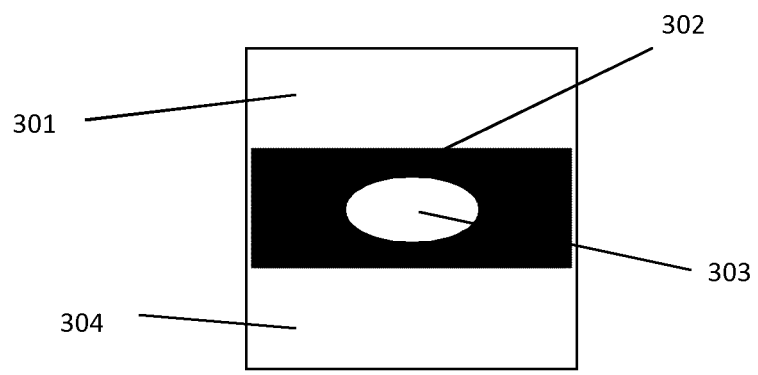
Figure 3a
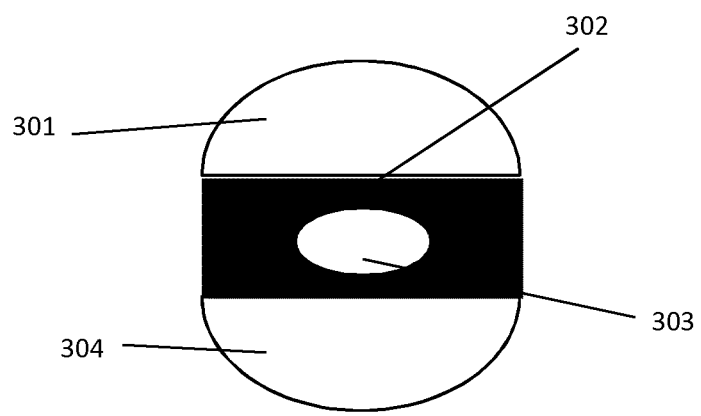
Figure 3b

FIGURE 4
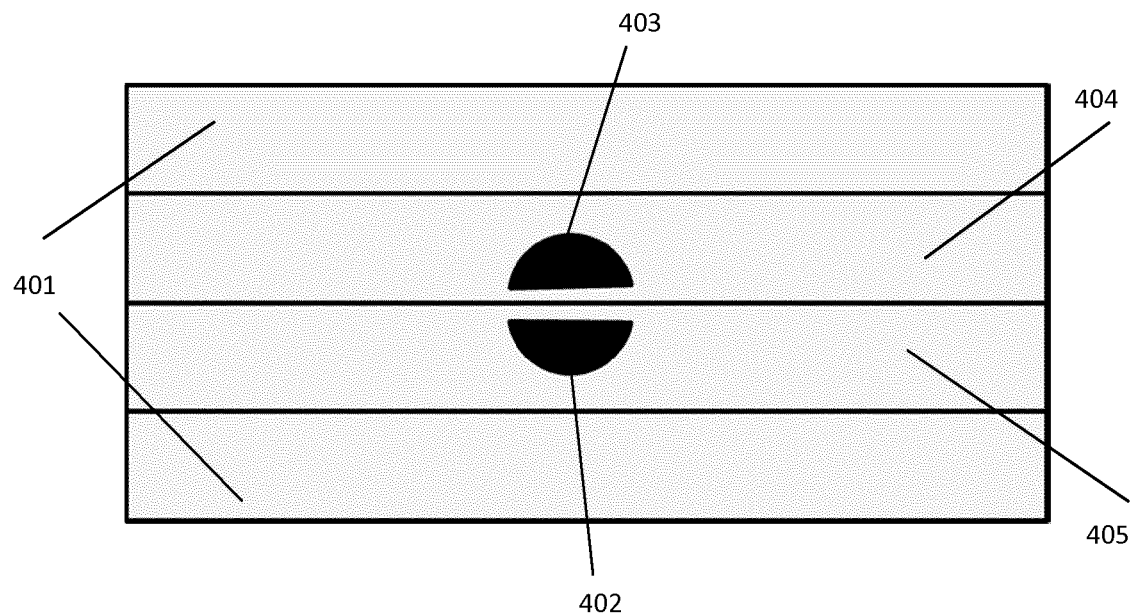
Figure 4a
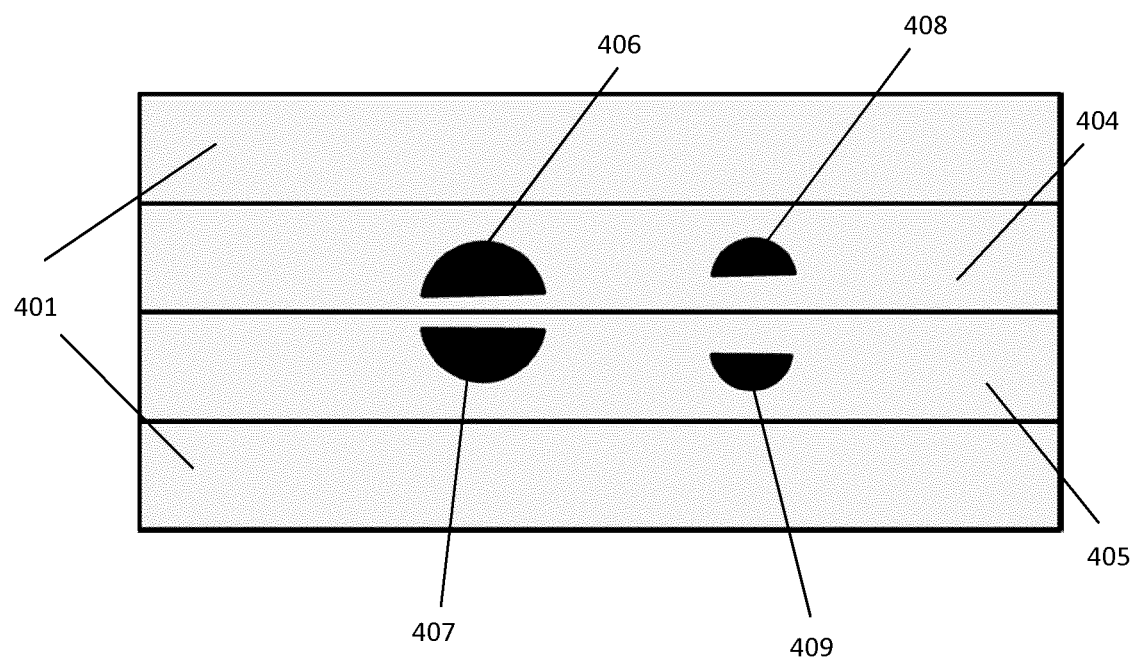
Figure 4b

METHOD AND APPARATUS FOR REDUCING SCATTERED LIGHT IN BROAD-LINE FUNDUS IMAGING

CROSS-REFERENCE TO RELATED APPLICATIONS

This application is a National Phase application under 35 U.S.C. § 371 of International Application No. PCT/EP2016/052287, filed Feb. 3, 2016, which claims priority to U.S. Provisional Patent Application No. 62/112,583, filed Feb. 5, 2015, the disclosure of each of which is hereby incorporated herein by reference in its entirety.

FIELD OF THE INVENTION

The embodiments presented herein concern the reduction or elimination of unwanted reflections during imaging of the fundus of the eye.

BACKGROUND

The basic design of most fundus imagers (both flood illuminating and scanning types) relies on a single concept that illuminating light is scattered by the retina (fundus) of the eye of a subject, and the return light is collected and detected. Thus, both illuminating and detected light must travel through the optical components of the eye, although not necessarily through common paths.

Diffuse and specular reflections from various optical components of the fundus imagers as well as the optical components of the eye such as the corneal and crystalline lens surface can contribute to unwanted light. Such scattered light can reduce the contrast required to detect low-level features in the fundus of an eye. For example, only about 1% of the incident light is scattered by the retinal tissue to contribute to the image, and of that, only about 1% is at angles that emerge from the pupil and are accessible for collection. Such a weak signal is easily overcome by the backscattered signal from the optical train of the instrument ($\sim 10^{-2}$) and even more so from the unwanted reflections from the cornea ($\sim 2 \times 10^{-2}$). Even when the components of the optical system (such as the scan lens and the objective lens) have proper antireflection coatings, the various contributions to the unwanted reflections, also known as artifacts, easily overwhelm that of the desired signal. Thus the elimination of these unwanted artifacts has consumed considerable design efforts in ophthalmic instrumentation. Some practical known methods are pupil-splitting, anti-reflection points, and confocal apertures.

Broad-line fundus imaging (see e.g. WO2014/140256 hereby incorporated by reference) is one type of scan-based fundus imaging technology impacted by reflection artifacts. Pupil splitting and dead zones between illumination and detection zones (where 'dead zones' indicate un-used zones for either illumination or imaging) have been applied to these systems to reduce the impact of artifacts to some success. FIG. 1 diagrams two possible design approaches to a broad-line fundus imager. Each design has separate paths for illumination and collection. Light passes through an illumination aperture and then travels towards the retina. Light returning from the retina travels along the collection path towards the detector passing through a collection aperture. The scan lens (101=SL) and the objective lens (102=OL) are indicated for reference. In FIG. 1a, the collection aperture 103 is fixed while in FIG. 1b, the collection aperture 104 is a hole in the galvo scanner so its size varies depending on the scanner position. The collection aperture and sensitive region on the detector together define the region between the collection rays where the light must originate to be detected. Note that in these diagrams, the separation between illumination and collection beams has been exaggerated. Typically, the pupil size is on the order of a few millimeters, thus the separation of illumination and collection rays will be about a millimeter apart on the lenses.

SUMMARY OF THE INVENTION

Embodiments described herein are directed to systems and methods for fundus imaging with specialized illumination control that allows for selective illumination patterns to be achieved at a pupil-splitting plane during imaging. A fundus imager according to the basic embodiment of the present application has a lens, a source of light for illuminating through the lens, a plurality of illumination paths from the source through the lens to the eye, optics for scanning the illumination paths so as to scan locations on the eye, a detection path from the eye through the lens, a detector for collecting light returning through the detection path from the eye and generating signals in response thereto, and a processor for generating an image from the detected signals. The imager includes selective illumination where light is delivered to the eye through a subset of the illumination paths while the optics scan the illumination path. This can be achieved through blocking a light path or by using an illumination source capable of illuminating separate areas at the pupil plane. While the most general system references a single lens, the concept applies to any one or plurality of optical components that are meant to transmit light but reflect some portion of the light. Examples include, but are not limited to, lenses, prisms, and diffractive optical elements. Using such an imaging device, it is possible to record high-resolution color fundus images with reduced visible artifacts such as reflections, haze and scatter.

BRIEF DESCRIPTION OF THE DRAWINGS

FIG. 1 depicts optical schematics of two prior art broad line fundus imaging (BLFI) systems that avoid overlap of the illuminating and collecting beams. FIG. 1a illustrates a system having a fixed collection aperture while FIG. 1b illustrates a system with a dynamic collection aperture realized by a hole in the galvanometer scanner.

FIG. 3 depicts one configuration of pupil splitting for a scan-based fundus imager. FIG. 3a shows a rectangle-O-rectangle structure that would be placed near the pupil plane of the system. FIG. 3b illustrates the D-O-D shaped regions that are imaged to the subject's pupil plane depending on the imaging configuration.

FIG. 4a illustrates a simulation of four stripes in the central part of a fundus image in the detector plane showing artifacts resulting from reflections from the illuminating light from a surface of the objective lens for the case of a lens surface causing an inverted image. FIG. 4b illustrates a simulation of the same central four stripes of a fundus image where one lens surface causes upright reflex artifacts while another lens surface forms inverted artifacts. FIG. 4c illustrates a simulation of two central stripes of a BLFI image collected using one aperture of the pupil splitting arrangement shown in FIG. 3a. FIG. 4d illustrates a simulation of the same two stripes as FIG. 4c using the other illumination aperture from FIG. 3a.

DETAILED DESCRIPTION

Figures 2, 2A:
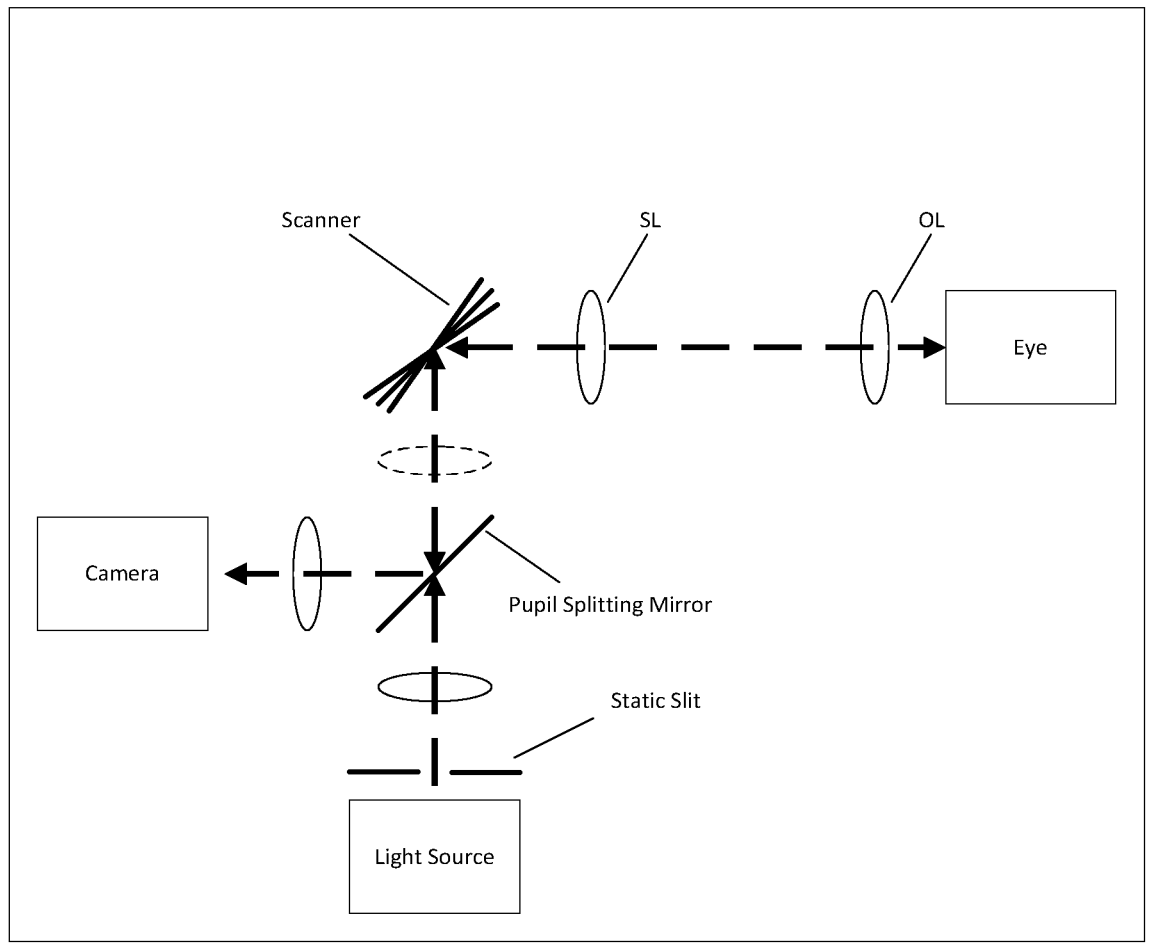
FIG. 2 depicts two prior art schematic diagrams of possible BLFI fundus imagers optical train designs.
FIG. 2a illustrates the basic components of a descanned system.

FIG. 2 illustrates the basic components of descanned (FIG. 2a) and imaged (FIG. 2b) broad line or slit-scanning fundus imagers as described in WO2014/140256 and hereby incorporated by reference. In both designs, light from a light source passes through an illumination aperture (slit) and travels through a series of lenses as it travels toward the eye. The abbreviation SL indicates the scan lens and OL indicates the ophthalmic or objective lens. A scanner is located in the illumination path to scan the light over a plurality of transverse locations on the eye. Light returning from the eye travels back along a portion of the illumination path towards a detector. The systems both contain pupil splitting mirrors that allow clean separation of the illumination and detection paths. There are multiple ways of achieving the illumination and collection apertures as would be appreciated by those skilled in the art.

In de-scanned detection as illustrated in FIG. 2a, the illumination light and light reflected or backscattered by the fundus will both be deflected by the scanner (or in some cases multiple scanners). In this arrangement, the illumination slit and the detector are aligned fixed to each other and the fundus will be effectively "scanned" over the pixels of the camera in stripe or strip shaped image portions. The stripes are then combined to produce a full image over a desired field of view.

Figure 2B:
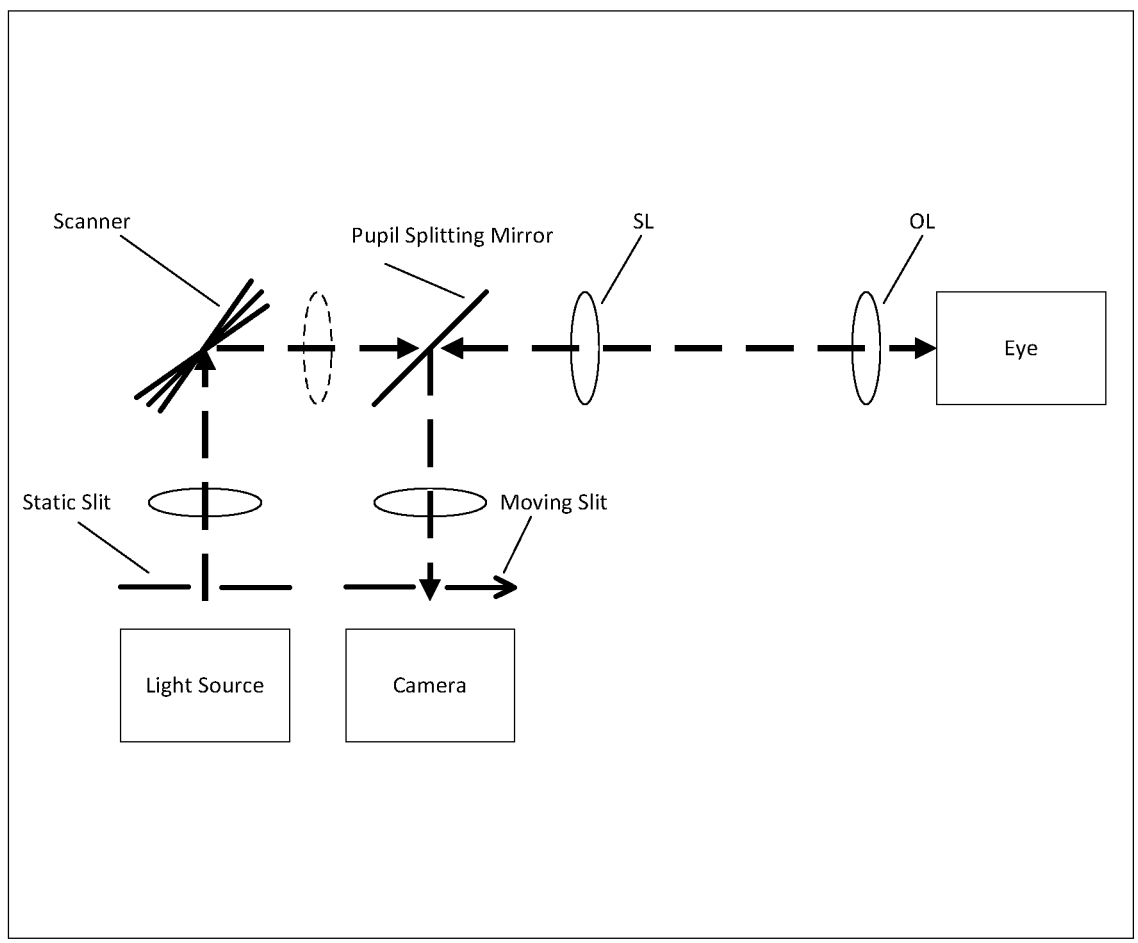
FIG. 2b illustrates the basic components of a non-descanned or imaged detection arrangement.

In non-descanned or imaged detection systems as illustrated in FIG. 2b, the entire image of the retina is built up in stripes on the camera with each position of the retina being uniquely mapped to a position on the camera and vice versa. In this type of configuration, only the illumination light is scanned and the light returning from the eye is split at the pupil splitting mirror in front of the scanner. A moving slit or aperture is positioned in front of the camera and is moved synchronously with the scanner. In an alternative approach, the slit could be static and the slit and camera could be moved together to realize the same effect. Alternatively some sort of electronic aperturing or shuttering of the camera could be employed.

Reflections from most optical surfaces used in laser scanning fundus imaging systems such as slit-scan fundus imagers described above can be minimized by selectively separating the illuminating light and that of the detecting or collecting beam. In line and slit scanning fundus imagers such as BLFI, this is best accomplished by minimizing the etendue of the illumination and collection light in one dimension, the short-dimension of the scanned line, and then selectively isolating portions of the pupil to separate illumination paths from collection paths (i.e., pupil splitting). Upon elimination of unwanted reflections, the final image obtained will be sharper and have greater contrast, thus low-contrast features obscured by scattered/unwanted light, will be more easily detectable.

This pupil-splitting approach works to first order for most optical surfaces, however, a cleaner separation between the illuminating and the collecting beams is required to address unwanted reflections from the ophthalmic/objective lens. An option to provide this cleaner separation between illumination and collection, especially effective for corneal lens reflex suppression, is to use illumination and detection areas where these areas are separated by dead zones which are not used by either the illumination or detection light and might actually be blocked by special apertures in the illumination respective of the detection paths. Stated differently, the pupil-splitting approach works well for reflecting surfaces conjugated to the pupil-splitting plane. However, in order to suppress all reflexes near the pupil-splitting plane, a dead zone is needed. In the axial direction, there are reflection free zones around the pupil-splitting plane. The extend of these zones is proportional to the dead zone width.

One example of such a pupil splitting arrangement is a rectangle-O-rectangle splitting structure as illustrated in FIG. 3a that can serve as the pupil splitting mirror in the two BLFI designs illustrated in FIG. 2 to address the unwanted reflections from the objective lens (OL) and/or suppress reflexes near the pupil-splitting plane. Locations at or near the pupil plane are illuminated via two rectangular-shaped illumination areas 301 and 304, which are separated from each other by a separating region or dead zone 302. This arrangement defines two illumination paths and one detection path in the system. The reflected light passes through area 303 completely within the separating region, in this case a slightly elliptical area, to separate it from the illumination light on its way to the detector. Other splitting configurations are known in the art. The shape and extent of the scan mirror can act as an aperture in the system, which is imaged at or near the pupil plane and can lead to certain scanning positions where the combined aperture of the octagonal scan mirror and the rectangular aperture seeming to resemble a trapezoid or other polygonal structure when viewing the pattern at the pupil plane. Furthermore, if the scan-mirror and rectangular aperture are not imaged into each other, it is not possible for both to be located exactly at a plane conjugate to the pupil. In this case, both are located near that plane at different positions and further are inclined to the optical axis so that the trapezoid or polygon aperture is not sharp in the pupil plane. This can lead to a perception that the trapezoid or polygon aperture is a D-shaped region as viewed at the pupil plane as illustrated in FIG. 3b. Similar to FIG. 3a, the illumination paths 301 and 304 and the detection path 303 are separated by a dead zone 302. The shape of reflections in the detection plane is an image of the intensity distribution of the pupil plane.

A scattered light analysis has revealed that there are two different types of objective lens reflections. One kind exists if the intermediate image of the retina behind the objective lens is located at the center of curvature of a surface of the objective lens (and in particular its anterior surface i.e., the one closer to a patient's eye). This reflection will be on the optical axis and will be reflected back in the system producing a bright spot on axis. Illumination points above the optical axis will then be reflected under the optical axis, so that the overall reflections are only visible in a very small region around the optical axis.

The other type of reflection occurs if the intermediate image of the retina is located on the posterior surface of the objective lens, the surface of the lens facing inside the instrument, which tends to be closer to the real image formed of the patient's retina). This reflex will be retroreflected, however, points above the optical axis will be reflected above that axis. Because of this, reflections are visible in larger areas around the optical axis. Such reflections cannot be effectively suppressed by the help of dead zones, as dark dead zones would appear sharply in the fundus images.

The basic idea of the embodiment proposed here is to selectively adjust the illumination pattern used during imaging. This can be accomplished in a number of ways as will be described in further detail below.

FIG. 4 depicts a simulation of four image stripes comprising the central portion of an image at the detector plane taken with a BLFI system employing the pupil splitting aperture illustrated in FIG. 3a. In general, the stripes can overlap, but they are shown here as non-overlapping for clarity. The width of the stripes is arbitrary. In FIG. 4a, light reflections 402 and 403 arising from the objective lens are visible in two image stripes 404 and 405. The upper and lower stripes 401 are perfectly free of scattered light. For the case of a lens surface causing an inverted image, illumination through aperture 301 is responsible for generating artifact 402 and illumination through aperture 304 is responsible for generating artifact 403.

Here we describe an approach to deal with these artifacts by selectively illuminating through only one of the two illumination paths depending on which portion or in this case, stripe, of the image is being collected. For the example shown in FIG. 4a, where the reflections appear inverted relative to the illumination aperture, during collection of stripe 404, the system is controlled so that light shall pass only through illumination aperture 304 resulting in an artifact free image stripe. Similarly, for collection of stripe 405, only aperture 301 is illuminated. For all other stripes besides the center two displaying reflections, both illumination apertures could be illuminated.

In general, more lens surfaces cause more reflections of the illumination, some upright and some inverted depending on the position and curvature of the lens surfaces. FIG. 4b depicts a situation where one lens surface reflects the illumination paths to form upright artifacts, 406 and 407, in the retinal image, while another lens surface has different position and curvature such that it reflects illumination paths to form inverted artifacts 408 and 409. The reflections are in general offset horizontally as shown, because the lens is in general slightly tilted from the nominal axis of symmetry of the illumination paths. In the situation illustrated in FIG. 4b, illumination from 304 is responsible for artifacts 407 and 408, the artifacts existing in different image stripes. The inverted reflections could also end up in the same stripe. Similarly, illumination from 301 is responsible for artifacts 406 and 409. The lenses are preferably tilted such that the artifacts (406 and 409) due to illumination through 301 are disjoint from the artifacts (407 and 408) due to illumination through 304.

Figure 4C:
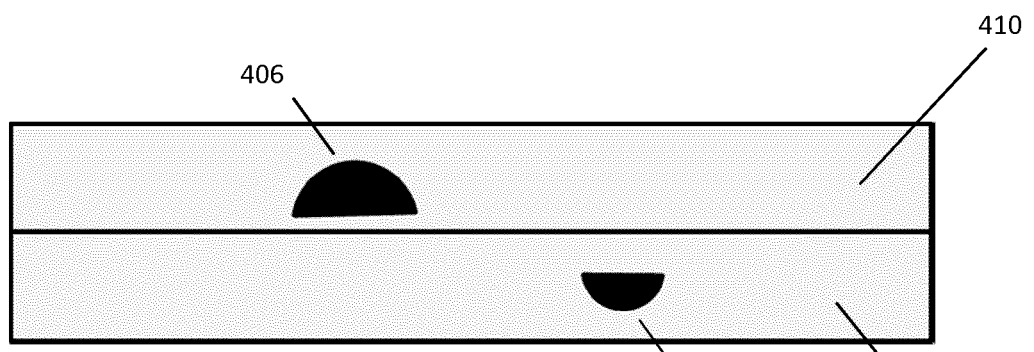
Figure 4D:
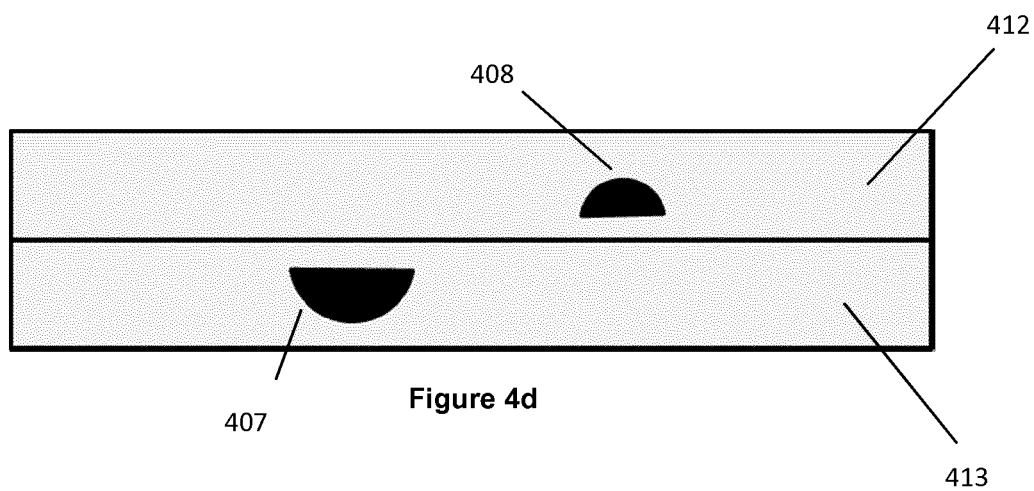

In such a situation where each illumination path produces reflections in several positions on the total retinal image, we can first illuminate through 301 to capture image stripes 410 and 411 as illustrated in FIG. 4c, and then illuminate through path 304 to capture image stripes 412 and 413 illustrated in FIG. 4d. There are areas on each of images that are corrupted by reflections, but these areas are disjoint, so by excluding the corrupted portions and merging the remainder of these two images in a processor a complete artifact-free image can be generated. This same general approach could be used if the reflections appear in the same or different stripes of the total image.

The sequence of selective illuminations can be used in both descanned imaging systems (e.g. FIG. 2a) where both the illumination and detection light is scanned and the images are collected on the same detector area and combined in a processor to yield the complete image and in non-descanned or imaged systems (e.g. FIG. 2b) where only the illumination light is scanned and the complete image is built up in real time using different regions on the detector. The idea could be generalized to any number of illumination paths.

As a result of selective illumination, the stripes imaged using only one illumination path will appear dimmer. This could easily be handled in post processing by counting the image stripes in the central region twice. Alternatively, the brightness or the integration time could be adjusted during acquisition for the stripes impacted by the reflexes to get the same image brightness for the whole fundus image. An alternative that achieves full exposure for most of stripes 404 and 405 is to illuminate stripes 404 and 405 sequentially along each illumination path in turn, acquiring images for each illumination path, one image suffering from a lens reflection. These two images are then combined so that the artifact-free portions have the full illumination brightness, and in the region where one image has an artifact, the pixels from the artifact-free images are brightened to match.

Figure 5:
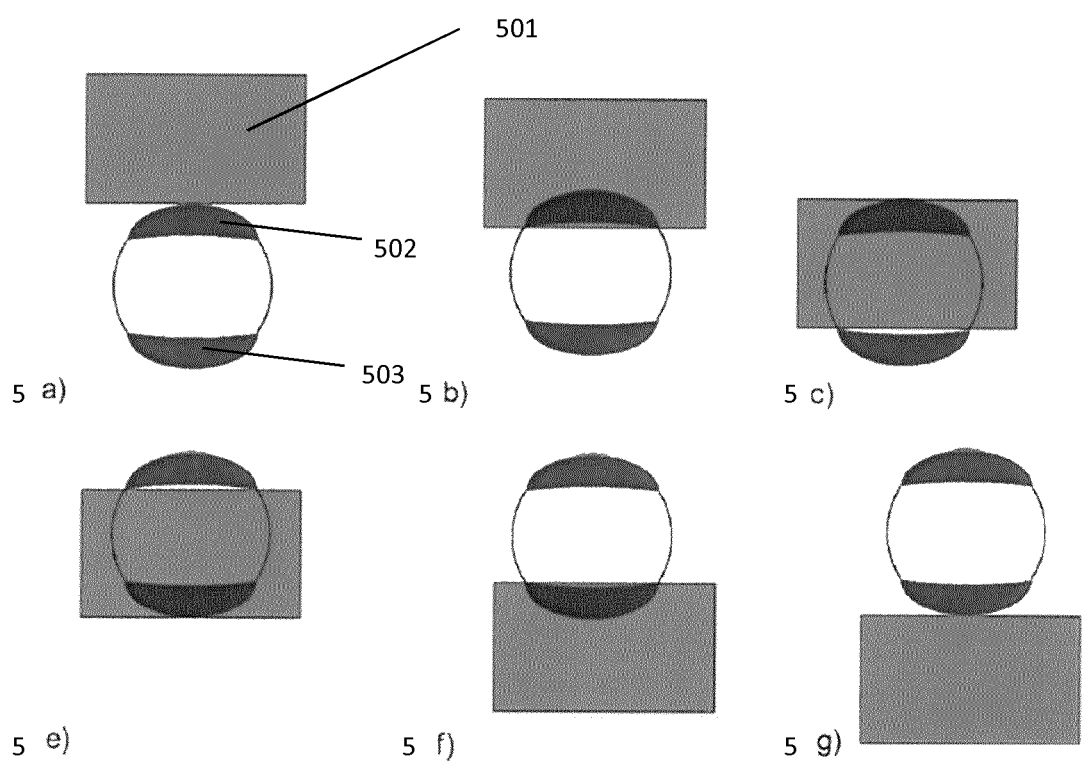
FIGS. 5a to 5c and 5e to 5g are a series of images demonstrating a sequence of selective illumination according to one aspect of the present application.

In some embodiments, the selective illumination can be realized using any kind of switchable optical element located in the illumination ray paths as close as possible to the pupil splitting element, that can be time controlled to block one of the illumination paths depending on the region of the fundus being illuminated. FIG. 5 shows a series of images for time-controlled selective blocking of the illumination in the sequence 5a) to 5c) and 5e to 5g). All of the stripes in the image above the optical axis, excepting the most central ones, should be acquired in state 5a), in which both the illumination circular-segments 502 and 503 are open (Item 501 in FIG. 5 refers to the blocking element). The integration for the stripe immediately above the optical axis should start in state 5b), and should be finished in state 5c). For the stripe immediately below the optical axis, the start time should be state 5e) and the stop time state 5f). The rest of the image should be acquired in state 5g) where both circular-segments are open again. This approach means that a certain dead time between 5c) and 5e) in the center of the images occurs where no integration should be taken.

While this particular embodiment shows a linear movement of a blade 501, a rotating element embodiment with equivalent effect would also be possible. In a preferred embodiment, the blocking could be done with a continuously rotating shutter wheel that is synchronized to the detection devices and sequentially blocks the desired parts of the pupil. A rotating wheel could be used for live movies/imaging because the shutter repeatedly blocks the portions of the illumination path. In addition, in yet still another embodiment, an LCD filter or a digital light processing (DLP) element can selectively block portions of the illumination in an electronically controlled manner. In this case, the switching could be realized with the implementation of two switchable LCD-elements or fast shutters. An advantage of this approach would be the lack of motors and associated gearing. Moreover, both the pupil splitting optics and the switchable shutter can be incorporated into a single LCD filter unit, in which the opacity of individual sectors of the LCD filter can be fully controlled from zero to one.

In alternative embodiments, the selective illumination can be realized by building an illumination source with separate selectively operable elements, one illuminating region 502 and one illuminating region 503 in FIG. 5. This arrangement would allow electronic, rather than mechanical, selection of the illumination sources, by selectively energizing only the element that illuminates the desired region.

More generally, some lenses in an ophthalmic imager could have surfaces angled to reflect illumination into the detection path to appear in regions far from the center of the image, for example reflections analogous to 402 and 403 in FIG. 4 but lying outside of stripes 404 or 405 in FIG. 4. The selective illumination can be used to remove such reflections, by blocking the portion of the illumination that causes the reflection for at least one sub-image capture of the affected region in the image. A second shutter on a wheel, or electronic selection of illumination sources, can supply the needed timing of partial illuminations.

The human eye reflects and scatters some light from its cornea and anterior surfaces. Usually these reflections are prevented from reaching the image sensor, but if due to misalignment of the eye they do corrupt the retinal image, reflections from illuminating light 502 and light 503 corrupt different locations in the retinal image. So long as the corrupted regions can be located on images acquired with each illumination separately, the data in these regions from the uncorrupted image can be used to build an artifact-free complete image.

Haze, scatter, and fluorescence from the human eye can also be avoided by selective illumination. For example, the eye lens fluoresces under the blue illumination that is useful in imaging the fluorescence of the retina. In slit-scan imaging, the lens fluorescence usually appears above and below the illuminated strip of retina, and out of focus. When imaging the superior retina, for example, the illumination 502 might overlap the view of fluorescing retina, while illumination 503 might interfere with imaging the inferior retina. An instrument with selective illumination can use illumination 503 alone while scanning the superior retina, illumination 502 alone while scanning the inferior retina, to collect views of the retina free of interfering lens fluorescence. Haze and scatter are similarly avoided whenever the scatter from the individual illumination sources corrupt disjoint regions of the retinal image.

With the described methods in combination with proper dimensioning of the dead zones between illumination and detection zones in the pupil splitting plane, the net result will be a system free of unwanted reflections, scattering, and haze such as those described herein above. The implementations in which the corrupting illumination is blocked or turned off, while scanning the region of retina that illumination would have corrupted, allow even a fully analog system to be produced, e.g., where the images are reflection-free and visible with the unaided human eye.

Figure 6:
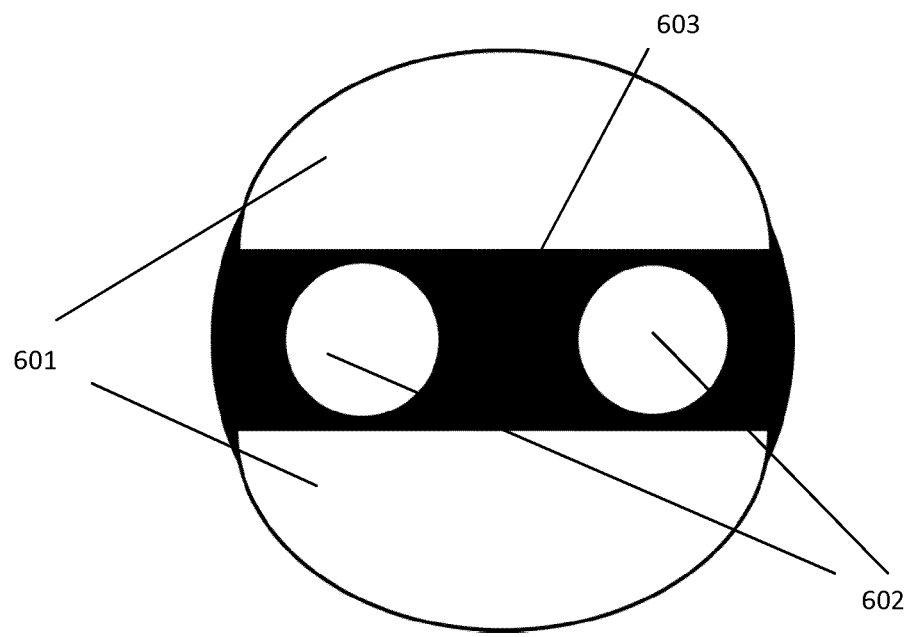
FIG. 6 depicts a possible pupil splitting configuration for a stereoscopic fundus system.

For special fundus imaging devices, such as stereoscopic microscopes, a reflection suppression mask as presented in FIG. 6, would easily be achievable. The illumination zones in this Figure are indicated as 601 and the detection zones 602. The change of this pattern from that of FIG. 3 is the existence of a second detection zone. The area between these indicated zones is a dead zone 603, where no light is allowed to pass.

The invention enables a fundus imager to image a fundus angle of at least 45 degrees in the absence of mydriatic drops and for non-dark-adapted eyes, i.e., for a pupil diameter of approximately 2 mm or larger. Although various applications and embodiments that incorporate the teachings of the present invention have been shown and described in detail herein, those skilled in the art can readily devise other varied embodiments that still incorporate these teachings.

The Following References are Hereby Incorporated by Reference:
  US20130222763
  WO2012059236
  WO2014/140256
  U.S. Pat. No. 4,135,791
  U.S. Pat. No. 4,170,398
  U.S. Pat. No. 4,732,466
  U.S. Pat. No. 8,488,895
  U.S. Pat. No. 8,814,362
  US Publication 20070031002

The invention claimed is:

1. A fundus imager for imaging an eye of a subject, comprising:
   a source of light for illuminating the retina through the pupil of the eye;
   a plurality of illumination regions at the pupil for light entering the eye;
   a single collection region at the pupil for returning light exiting the eye, wherein returning light due to multiple of said illumination regions is collected through said single collection region;
   a detector for collecting light returning from the eye and generating signals in response thereto;
   a processor for generating an image of the retina from the signals;
   means to selectively illuminate the retina through each of the plurality of illumination regions, wherein for some locations on the retina, the pupil regions are illuminated simultaneously and for other locations on the retina, the pupil regions are illuminated sequentially wherein said processor selectively merges portions of the signals associated with the various illumination paths to generate a single composite image with reduced artifacts.

2. A fundus imager as recited in claim 1, wherein the selective illumination means is a switchable element for selectively blocking one of the illumination regions at a time.

3. A fundus imager as recited in claim 2, wherein the switchable element is a rotating shutter wheel.

4. A fundus imager as recited in claim 2, wherein the switchable element is a blade.

5. A fundus imager as recited in claim 2, wherein the switchable element is an LCD or OLP filter.

6. A fundus imager as recited in claim 1, wherein light entering the eye is scanned across the retina.

7. A fundus imager as recited in claim 6, wherein the light entering the eye is scanned using a moving slit in front of the beam of light.

8. A fundus imager as recited in claim 6, wherein the light entering the eye is scanned using a transverse movement of the beam of light.

9. A fundus imager as recited in claim 6 wherein the fundus imager is descanned.

10. A fundus imager as recited in claim 1, wherein the selective illumination means is an illumination source with separate selectively operable elements.

11. A fundus imager as recited in claim 1, wherein the fundus imager is a broad line fundus imager.

12. A method to control the illumination in a fundus imaging system having illumination and detection paths, said method comprising:
   separating the illumination and detection paths at a plane conjugate to the pupil of an eye using at least three non-overlapping light transmittable zones, wherein a first zone and a second zone of the three non-overlapping light transmittable zones define illumination regions at the pupil of the eye to transmit light into the eye and a third zone defines a single collection region at the pupil of the eye wherein returning light exiting the eye due to the first and second zones is collected through said single collection region;

for some locations on the retina, sequentially scanning the light through the first zone alone and then through the second zone alone, while collecting light through the third zone to obtain signals corresponding to two different images of the same location on the retina, the first image being associated with the illumination through the first zone and a second image being associated with the illumination through the second zone;

for other locations on the retina, scanning the light through the first and second zones simultaneously while collecting light through the third zone to obtain a third image of a different location of the retina; and assembling a single composite image of the fundus by selectively merging the signals corresponding to the first, second and third images to reduce artifacts in the single composite image.

13. A method as recited in claim 12, further comprising illuminating through either the first zone or the second zone, wherein time for collecting the light through the third zone is adjusted based on said illumination.

14. A method of imaging the eye of a subject, comprising:
scanning illuminating light across retinal locations in the eye, the illuminating light passing through a plurality of illumination regions at the pupil wherein for some first locations on the retina, multiple regions at the pupil are simultaneously illuminated and for some second locations on the retina, the individual regions at the pupil are sequentially illuminated;

detecting light returning from the eye through a single collection region at the pupil and generating signals in response thereto for the first and second retinal locations of the eye illuminated by the illumination regions wherein for the second locations on the retina, the signals correspond to multiple images of the same location of the eye, each image associated with a different illumination region; and combining the signals to generate a single composite image of the eye wherein portions of the signals associated with various illumination regions are selectively merged to reduce artifacts in the image.

15. A method as recited in claim 14, further comprising compensating for reduced intensity of the signals detected associated with the second locations.

16. A method as recited in claim 14, where the illuminating light covers a slit shaped area on the retina of the eye.

17. A fundus imager as recited in claim 6, wherein the light entering the eye is scanned using a scanner.

18. A fundus imager as recited in claim 1, wherein the pupil regions are illuminated sequentially at central locations of the retina and simultaneously for other locations of the retina.

19. A method as recited in claim 12, wherein light is scanned sequentially through the first zone and second zone when imaging central locations of the retina, and scanned simultaneously through the first zone and second zone when imaging other locations of the retina.

20. A method as recited in claim 14, wherein the second locations are at central locations of the retina and the first locations are at other locations of the retina.

* * * * *